US007098345B2

(12) United States Patent
Molnar et al.

(10) Patent No.: US 7,098,345 B2
(45) Date of Patent: Aug. 29, 2006

(54) PROCESS FOR PREPARING 1,2,3,9-TETRAHYDRO-9-METHYL-3-[(2-METHYL-1H-IMIDAZOL-1-YL)METHYL]-4H-CARBAZOL-4-ONE

(75) Inventors: Sandor Molnar, Debrecen (HU); Csaba Szabo, Debrecen (HU); Erzsebet Meszaros Sos, Debrecen (HU); Szabolcs Salyi, Debrecen (HU); Tivadar Tamas, Debrecen (HU)

(73) Assignee: TEVA Gyógyszergyár Zárköruen Müködö Részvénytársaság, Debrecen (HU)

( * ) Notice: Subject to any disclaimer, the term of this patent is extended or adjusted under 35 U.S.C. 154(b) by 234 days.

(21) Appl. No.: 10/425,450

(22) Filed: Apr. 29, 2003

(65) Prior Publication Data
US 2005/0020655 A1 Jan. 27, 2005

Related U.S. Application Data

(60) Provisional application No. 60/376,323, filed on Apr. 29, 2002.

(51) Int. Cl.
C07D 233/58 (2006.01)
(52) U.S. Cl. .................................. 548/311.4
(58) Field of Classification Search .............. 548/346.1
See application file for complete search history.

(56) References Cited

U.S. PATENT DOCUMENTS

| 4,695,578 | A | * | 9/1987 | Coates et al. ............... 514/397 |
| 4,725,615 | A | * | 2/1988 | Coates et al. ............... 514/397 |
| 4,739,072 | A | | 4/1988 | Oxford et al. |
| 4,749,718 | A | | 6/1988 | Coates et al. |
| 4,783,478 | A | | 11/1988 | Wootton et al. |
| 4,835,173 | A | | 5/1989 | Tyers |
| 4,859,662 | A | | 8/1989 | Coates et al. |
| 4,957,609 | A | | 9/1990 | Godfrey et al. |
| 4,983,621 | A | * | 1/1991 | Bunce et al. ............... 514/397 |
| 5,344,658 | A | | 9/1994 | Collin |
| 5,478,949 | A | | 12/1995 | Bod et al. |
| 5,622,720 | A | | 4/1997 | Collin |
| 5,629,333 | A | | 5/1997 | Young |
| 5,712,302 | A | | 1/1998 | Young |
| 5,854,270 | A | | 12/1998 | Gambhir |
| 5,962,494 | A | | 10/1999 | Young |
| 6,063,802 | A | | 5/2000 | Winterborn |
| 6,388,091 | B1 | | 5/2002 | Lee et al. |
| 2004/0019093 | A1 | | 1/2004 | Aronhime et al. |

FOREIGN PATENT DOCUMENTS

CN 1113234 A 12/1995

| EP | 0 415 522 B1 | 3/1991 |
| EP | 0 276 559 B1 | 8/1998 |
| GB | 2 153 821 | 8/1985 |
| WO | WO 02/36558 A2 | 5/2002 |
| WO | WO 02/055492 A2 | 7/2002 |
| WO | WO 03/090730 A1 | 11/2003 |

OTHER PUBLICATIONS

Iida et al. "Intramolecular Cyclization of Enaminones Involving Arylpalladium Complexes. Synthesis of Carbazoles" J. Org. Chem. 1980, vol. 45, p. 2938-2942.
European Pharmacopoeia 4.4, "Ondansetron Hydrochloride Dihydrate" p. 3489-91, 2003.
U.S. Appl. No. 10/425,210, filed Apr. 29, 2003 "Novel Crystal Forms of Ondansetron, Processes for their Preparation, Pharmaceutical Compositions Containing the Novel Forms and Methods for Treating Nausea Using Them".
Pirttimaki, J., et al. The Transformation of Anhydrate and Hydrate Forms of Caffeine at 100% RH and 0% RH, *European Journal of Pharmaceutical Sciences*, 1994, vol. 1, pp. 203-208.
Llacer, J.M., et al., "Formation of Ondansetrom Polymorphs" *International Journal of Pharmaceutics*, 1999, vol. 177, pp. 221-229.
Harry G. Brittain (Ed.) (1999) "Polymorphism in Pharmaceutical Solids" Drugs and the Pharmaceutical Sciences vol. 95, pp. 183-226, Marcel Dekker, Inc. New York, New York.
Byrn, S.R., et al. (Ed.) (1999) "Solid-State Chemistry of Drugs" Second Edition, pp. 59-67, SSCI, Inc. West Lafayette, Indiana.
Byrn, S.R., et al. (Ed.) (1982) "Solid-State Chemistry of Drugs" pp. 6-7, Academic Press, New York, New York.
Threlfall, T.L., et al. "Analysis of Organic Polymorphs" *The Analyst*, 1995, vol. 120, pp. 2435-2460.
Carless, J.E., et al. "Cortisone acetate crystals forms" *J. Pharm. And Pharmacology*, 1966, vol. 18, pp. 190S-197S.
Chen, Chem Abstr., "Synthesis of Antiemetic Ondansetron" Chinese J. of Pharmaceuticals, 1993, 24(6), pp. 241-242 (Ch).
The United States Pharmacopeia (USP 27-NF22), 22$^{nd}$ edition, First Supplement, Apr. 2004, pp. 3030, 3075-3076.
The United States Pharmacopeia (USP 27-NF22), 22$^{nd}$ edition, Second Supplement, Aug. 2004, pp. 3234, 3283-3285.
The United States Pharmacopeia (USP 26-NF21), 21$^{st}$ edition, The National Formulary, Jan. 2003, pp. 1351-1352.
The Merck Index p. 6977 "Ondansetron", 1996.
Grunberg, S.M., et al., "Control of Chemotherapy-Induced emesis," *N. Engl. J. Med.*, 1993, vol. 329, p. 1790-96.
Kim, M. Y, et al. "An Efficient Process of Ondansetron Synthesis" *Heterocycles*, 1997, vol. 45, No. 10, p. 2041-2043.

* cited by examiner

*Primary Examiner*—Kamal A. Saeed
*Assistant Examiner*—Nyeemah Grazier
(74) *Attorney, Agent, or Firm*—Kenyon & Kenyon LLP

(57) ABSTRACT

A process for preparing ondansetron by transamination of an ondansetron structural analog that can be readily prepared conveniently by a Mannich reaction is provided. The process represents an improvement upon known procedures for making ondansetron by transamination because of its rapid rate, selectivity and the ease with which the product can be isolated from the reaction mixture.

22 Claims, No Drawings

PROCESS FOR PREPARING 1,2,3,9-TETRAHYDRO-9-METHYL-3-[(2-METHYL-1H-IMIDAZOL-1-YL)METHYL]-4H-CARBAZOL-4-ONE

CROSS REFERENCE TO RELATED APPLICATION

This application claims the benefit under 35 U.S.C. 1.119 (e) of Provisional Application Ser. No. 60/376,323, filed Apr. 29, 2002, and is incorporated herein by references.

FIELD OF THE INVENTION

The present invention relates to the antiemetic drug ondansetron and its pharmaceutically acceptable acid addition salts, and more particularly to late stage process steps for synthesizing ondansetron.

BACKGROUND OF THE INVENTION

Ondansetron, whose systematic chemical name is 1,2,3,9-tetrahydro-9-methyl-3-[(2-methyl-1H-imidazol-1-yl)methyl]-4H-carbazol-4-one, and whose molecular formula is

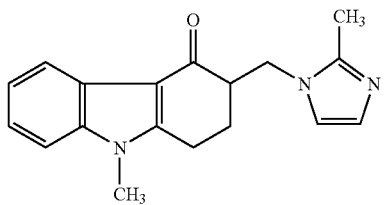

(I)

is the active ingredient of FDA approved antiemetic drugs that are indicated for treatment of nausea and vomiting associated with some cancer chemotherapy and radiotherapy and for the prevention of postoperative nausea and/or vomiting. Ondansetron is commercially available in orally disintegrating tablets and ondansetron hydrochloride dihydrate is commercially available in tablets and in oral solution, each under the brand name Zofran®.

Ondansetron has one chiral center. Ondansetron was first disclosed as a racemate in the patent literature in U.S. Pat. No. 4,695,578 ("the '578 patent") in 1987. The '578 patent describes several ways by which ondansetron can be made. In Example 7 of the '578 patent, ondansetron was prepared by treating a 0.34 M solution of the hydrochloride salt of 3-[(dimethylamino)methyl]-1,2,3,9-tetrahydro-9-methyl-4H-carbazol-4-one of formula (IIa):

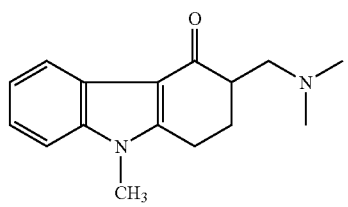

(IIa)

in water with 2.9 equivalents of 2-methylimidazole of formula (III):

(III)

The reaction was conducted at about 100° C. and required 20 hours to go to completion. Ondansetron was obtained in 82% yield after a single recrystallization. According to a general discussion of this reaction contained in the '578 patent, it may be carried out in a suitable solvent such as water or an alcohol, e.g. methanol, or mixtures thereof and at a temperature of from 20° to 150° C.

In Example 4 of the '578 patent, ondansetron was prepared by N-methylation of 1,2,3,9-Tetrahydro-3-[(2-methyl-1H-imidazol-1-yl)methyl]-4H-carbazol-4-one of formula (IV):

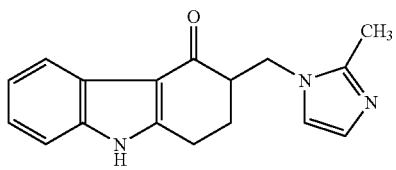

(IV)

A solution of the formula (IV) compound in dry N,N-dimethylformamide was added to a solution of sodium hydride in dry dimethylformamide to deprotonate the 1,2,3,9 tetrahydrocarbazol-4-one ring nitrogen and then the resulting anion was reacted with dimethylsulfate. The yield of the reaction was only about 21%. According to a general discussion of this reaction contained in the '578 patent, the reaction can be carried out in an inert organic solvent such as an amide, e.g. dimethylformamide; an ether, e.g. tetrahydrofuran; or an aromatic hydrocarbon, e.g. toluene.

Other preparations of ondansetron disclosed in the '578 patent include Example 8, where ondansetron was prepared by Michael-type addition of 2-methylimidazole to 9-methyl-3-methylene-1,2,3,9-tetrahydro-4H-carbazol-4-one of formula (V)

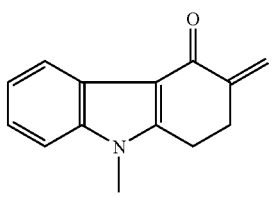

(V)

The reaction was conducted in refluxing water over a 20 hour period and occurred in 44% yield. According to a general discussion of this reaction in the '578 patent, suitable solvents include water; esters, e.g. ethyl acetate; ketones, e.g. acetone, or methylisobutylketone; amides, e.g. dimethylformamide; alcohols, e.g. ethanol; and ethers, e.g. dioxane or tetrahydrofuran; or mixtures thereof.

In Example 18(ii) of the '578 patent, ondansetron was prepared by substitution of 2-methyl-1H-imidazole for chloride in 3-(chloromethyl)-1,2,3,9-tetrahydro-9-methyl-4H-carbazol-4-one of formula (VI):

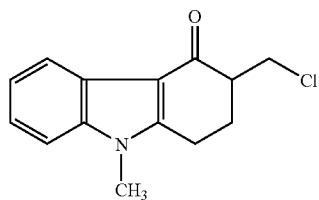

(VI)

The reactants were stirred in dry DMF under nitrogen at 90° C. for 3.75 hours. The reaction occurred in about 72% yield. According to a general discussion of this reaction contained in the '578 patent, it can be carried out in an amide solvent, e.g. dimethylformamide; an alcohol, e.g. methanol or industrial methylated spirit; or a haloalkane, e.g. dichloromethane.

In Example 19 of the '578 patent, 2,3,4,9-tetrahydro-9-methyl-3-[(2-methyl-1H-imidazol-1-yl)methyl]-1H-carbazole maleate of formula (VII):

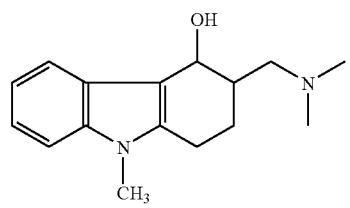

(VII)

was oxidized by 2,3-dichloro-5,6-dicyano-1,4-benzoquinone (DDQ) in dry THF and the counterion was separated to give ondansetron in 55% yield.

In Example 20, DDQ was used to oxidize 2,3,4,9-tetrahydro-9-methyl-3-[(2-methyl-1H-imidazol-1-yl)methyl]-1H-carbazol-4-ol of formula (VIII):

(VIII)

in 41% % yield (the '578 patent actually reports a yield corresponding to a 413% theoretical yield. The most likely explanation for the error is omission of a decimal place after the decimal point of the mass yield. Thus, we infer that the actual yield was 41%). According to a general discussion in the '578 patent, the oxidation reactions of Examples 19 and 20 may be conducted in ketones, e.g. acetone or butanone; ethers e.g. tetrahydrofuran or dioxane; amides, e.g. dimethylformamide; alcohols, e.g. methanol; hydrocarbons, e.g. benzene or toluene; halogenated hydrocarbons, e.g. dichloromethane; and water or mixtures thereof.

U.S. Pat. No. 5,478,949 discloses a multistep process for preparing ondansetron that concludes with the step of N-alkylating the methylene group alpha to the oxo group of the 1,2,3,9 tetrahydrocarbazol-4-one ring system of the compound of formula (IX)

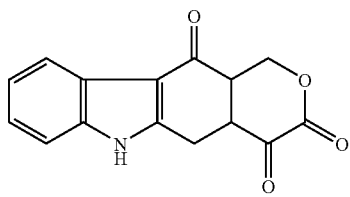

(IX)

with 2-methylimidazole to give a compound of formula (X):

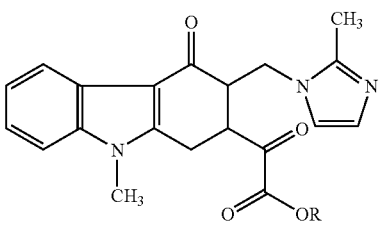

(X)

which is converted in situ to ondansetron by cleaving the oxalate group with a second nucleophile (EtO⁻) that also is present in the reaction mixture. The calculated theoretical yields ranged from 75% to 87.3%.

U.S. Pat. No. 6,388,091 discloses a process for preparing ondansetron wherein the silyl enol ether of 1,2,3,9-tetrahydro-9-methyl-4H-carbazol-4-one of formula (XI):

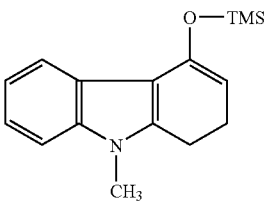

(XI)

is alkylated with a 1-(N,N-dialkylaminomethyl)-2-methylimidazole of formula (XII):

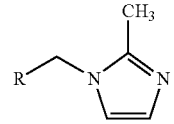

(XII)

where substituent R is N,N-dimethylamino, N,N-diethylamino, N,N-dipropylamino, morpholin-4-yl, piperidin-1-yl or pirrolidin-1-yl. According to the '091 patent, the reaction can be performed in an organic solvent such as methylene chloride, chloroform, acetonitrile, tetrahydrofuran, 1,4-dioxane, toluene, N,N-dimethylformamide, ethanol and a mixture thereof, or in a mixture of one of the above organic solvents and water to induce precipitation of the product. In the Examples, ondansetron was recovered in 81–86% yield.

U.S. Pat. No. 4,957,609 describes a process for preparing ondansetron and related compounds wherein the last step is closure of the central ring of the 1,2,3,9-tetrahydrocarbazol-4-one ring system starting with a compound of formula (XIII):

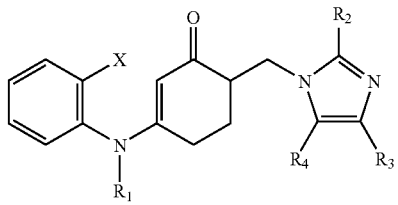

(XIII)

wherein X is a hydrogen or a halogen atom using a copper or palladium catalyst depending upon the identity of substituent X. When a palladium catalyst is used, suitable solvents include nitriles, e.g. acetonitrile, alcohols e.g. methanol or ethanol, amides, e.g. dimethylformamide, N-methylpyrrolidone or hexamethylphosphoramide, and water. When a copper catalyst is used, suitable solvents include amides, e.g. dimethylformamide, N-methylpyrrolidone or hexamethylphosphoramide, nitriles, e.g. acetonitrile, and alcohols, e.g. ethanol.

U.S. Pat. No. 4,739,072 describes another cyclization process for preparing ondansetron and related compounds. In this process, cyclization of the starting material, a hydrazine of formula (XIV),

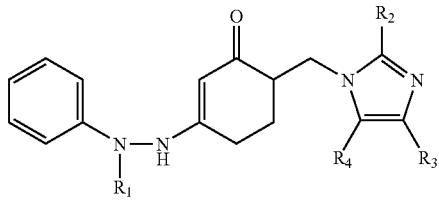

(XIV)

is induced with an acid. The Lewis acid $ZnCl_2$ was used in the examples. According to the '072 patent, the reaction can be performed in an aqueous medium, which may be aqueous alcohol (e.g. methanol, ethanol or isopropanol) or an aqueous ether (e.g. dioxane or tetrahydrofuran) as well as mixtures of such solvents. Anhydrous reaction media in which the cyclization can be conducted include one or more alcohols or ethers, carboxylic acids (e.g. acetic acid) or esters (e.g. ethyl acetate).

Chinese Patent Application No. 11143234 discloses additional one-step processes for preparing ondansetron which are related in that they install the (2-methyl imidazolyl) methylene group on the 1,2,3,9-tetrahydrocarbazol-4-one ring system.

It will be appreciated that considerable effort has been expended by synthetic chemists to discover a process for preparing ondansetron that represents an improvement over the processes described in the '578 patent. In fact, the preceding discussion of ondansetron preparation processes focuses on the final step of what, in many instances, are lengthy synthetic sequences from commercially available starting materials to ondansetron. The present invention arose out of our efforts to achieve improved results over those obtained in the '578 patent with a process that was well suited for scale up and industrial production of ondansetron without abandoning the basic synthetic strategies offered in the '578 patent. Accordingly, disclosed herein are improvements to the transamination process of compound (IIa) and related compounds that increase the reaction rate, yield and the general economic efficiency of producing ondansetron from such compounds.

SUMMARY OF THE INVENTION

We have discovered a process for preparing ondansetron by transamination which improves upon known processes for preparing ondansetron in terms of rate of the reaction, yield, selectivity and the ease with which ondansetron can be separated from the reaction mixture. In the process of the invention, a 3-[(dialkylamino)methyl]-1,2,3,9-tetrahydro-9-methyl-4H-carbazol-4-one undergoes transamination with 2-methylimidazole in a solvent system containing water and N,N-dimethylformamide. Once the reaction is complete, ondansetron can be separated from unreacted starting material, solvent and side products conveniently by cooling to induce crystallization followed by conventional physical separation of the solid from the liquid reaction mixture.

In addition to the process itself, the present invention further provides ondansetron and pharmaceutically acceptable ondansetron acid addition salts prepared by the inventive process.

Pharmaceutical products such as orally disintegrating tablets containing ondansetron, and conventional tablets and oral solutions containing pharmaceutically acceptable ondansetron acid addition salts also are provided.

DESCRIPTION OF THE PREFERRED EMBODIMENTS

The present invention provides a process for preparing ondansetron (I) by contacting a 3-[(dialkylamino)methyl]-1,2,3,9-tetrahydro-9-methyl-4H-carbazol-4-one of formula (II)

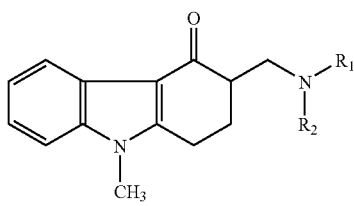

(II)

or salt thereof, wherein substituents $R_1$ and $R_2$ are independently selected from $C_1$–$C_6$ linear, branched and cyclic alkyl groups, with 2-methylimidazole in an especially advantageous solvent system whose discovery constitutes a part of the present invention. Preferably, alkyl moieties $R_1$ and $R_2$ are both methyl. Accordingly, an especially preferred starting material is 3-[(dimethylamino) methyl]-1,2,3,9-tetrahydro-9-methyl-4H-carbazol-4-one (IIa). The 3-[(dialkylamino)methyl]-1,2,3,9-tetrahydro-9-methyl-4H-carbazol-4-one of formula (II) is preferably added to the solvent system as a salt, yet more preferably as a hydrochloride salt.

Whereas ondansetron has a single chiral center, the process of this invention is useful for preparing either ondansetron enantiomer independently starting with an optically pure R or S-[(dialkylamino)methyl]-1,2,3,9-tetrahydro-9-methyl-4H-carbazol-4-one, and is useful for preparing racemic as well as non-racemic mixtures of ondansetron enantiomers starting from optically impure and racemic mixtures of R and S [(dialkylamino)methyl]-1,2,3,9-tetrahydro-9-methyl-4H-carbazol-4-ones.

A solvent system in accordance with this invention is a mixture of water and N,N-dimethylformamide ("DMF") and optionally other liquids. Mixtures of these two components contain more than trace amounts of each component. In contrast, pure DMF that has been stored in an unsealed container in a moist environment causing it to absorb moisture would not serve as a suitable solvent system in accordance with this invention. Thus, solvent systems of this invention contain from about 1% to about 99% DMF and from about 1% to about 99% water. Preferred solvent systems contain from about 10% to about 40% DMF and from about 50% to about 90% water. Especially preferred solvent systems contain from about 20% to about 33% DMF and about 66% to about 80% water. These ranges, preferred ranges and especially preferred ranges are expressed in terms of the volumetric amount of each component in pure condition that is used to formulate the solvent system.

The other organic starting material consumed in the process is 2-methylimidazole. 2-Methylimidazole is preferably supplied to the reaction mixture in molar excess over 1,2,3,9-tetrahydrocarbazol-4-one (II), more preferably in an amount of from about 2 to about 6 molar equivalents.

The solvent system of the present invention enables the use of higher temperatures to transform 1,2,3,9-tetrahydrocarbazol-4-one (II) to ondansetron than are attainable without pressurized vessels when water alone is used as a solvent as taught by the '578 patent. Preferred temperature ranges for the reaction are from about 95° C. to about 110° C., more preferably from about 100° C. to about 105° C., and most preferably the reflux temperature at ambient pressure of the particular solvent system used.

One advantage of the present invention is faster reaction times, which we attribute to the well recognized effect that solvent can have on the transition state of elementary reaction steps and to some extent upon acceleration of the reaction rate by higher temperature. As can be seen in the Examples, the reaction goes to completion in about 5 to 6 hours, instead of the 20 hours required when 1,2,3,9-tetrahydrocarbazol-4-one (IIa) is reacted with 2-methylimidazole in pure water. The increased rate of reaction is achieved without sacrificing yield or concomitantly producing new side products or significantly increasing the quantity of side products that must be separated. On the contrary, one side product, actually considered to be an intermediate of the reaction, is significantly reduced.

There occurs in the process of this invention and the processes of Examples 7 and 18(ii) of U.S. Pat. No. 4,695,578 an elimination reaction which produces the compound of formula (V), above, 9-methyl-3-methylene-1,2,3,9-tetrahydro-4H-carbazol-4-one (hereafter referred to as the "exomethylene carbazolone"). The exomethylene carbazolone is reactive toward Michael addition by 2-methylimidazole as demonstrated by U.S. Pat. No. 4,695,578, where it was used as a starting material for making ondansetron. Although not intending to limit the invention to any particular theory, it is believed that the exomethylene carbazolone is an intermediate in the predominant mechanism of the reaction of compounds of formula (II) and 2-methylimidazole leading to ondansetron. We have observed the exomethylene carbazolone in reactions conducted according to Example 7 of U.S. Pat. No. 4,695,578 well after the 3-dialkylaminomethyl starting material has been consumed.

The *European Pharmacopeia* requires that pharmaceutical grade ondansetron contain not more than 0.1% exomethylene carbazolone. *European Pharmacopeia* 4.4, p. 3490. This has proven to be a challenging standard to meet and there remains a need for an improved process for preparing ondansetron that minimizes its presence in the final product. We have discovered that under the temperature conditions and the preferred ratio of starting materials, i.e. 2–6 molar equivalents of 2-methyl imidazole, the exomethylene carbazolone, as well as the dimethylamine derivative of formula (II) can be completely consumed in about 6 hours resulting in a purer product and higher yield than obtainable either by Michael addition in prior art processes.

Turning to more particular details of a procedure by which the process may be practiced, the organic starting materials can be added to the solvent system at room temperature, although they also may be added at elevated temperature. Once all the 1,2,3,9-tetrahydrocarbazol-4-one (II) has dissolved, the amount of solvent versus 1,2,3,9-tetrahydrocarbazol-4-one (II) preferably is such as will produce a solution whose 1,2,3,9-tetrahydro-carbazol-4-one (II) concentration is from about 0.2 to about 0.5 Molar, although higher and lower concentrations may used. When the 1,2,3,9-tetrahydrocarbazol-4-one (II) and 2-methylimidazole are added to the solvent system at room temperature and in the preferred quantities (fully set forth above) the mixture will not necessarily be homogeneous or capable of becoming homogeneous at room temperature. Nevertheless, upon heating to a temperature within the preferred reaction temperature range, the starting materials will dissolve and be consumed. In fact, when operating at lower temperatures, dissolved starting materials in a heterogeneous mixture will still react, enabling further starting material to dissolve and continue the reaction. Thus, the process can, if desired, be practiced using a physically heterogeneous mixture containing undissolved starting materials and/or precipitated product. However, the preferred mode for practicing the inventive process is with heating and formation of a homogeneous mixture.

In addition to accelerating the reaction rate of transamination of compounds of formula (II) with 2-methylimidazole, the solvent system is well suited for crystallizing ondansetron. Thus, after the reaction has gone substantially to completion, ondansetron can be separated from the reaction mixture by cooling the solvent system to induce crystallization of ondansetron. The solvent system and soluble unreacted starting material and side products can be removed conventionally by filtration or decantation and then the crystals of ondansetron may be washed with a volatile liquid in which ondansetron is not appreciably soluble. It should be noted that when an excess of 2-methylimidazole is used and the starting materials are added in amounts corresponding to the preferred molar equivalents ranges and concentrations, that ondansetron can be crystallized from the reaction mixture without significant contamination by unreacted 2-methylimidazole. Alternatively, ondansetron may be separated from the reaction mixture by evaporating the solvent system and separating ondansetron from non-volatile substances in the reaction mixture e.g. by chromatography or by recrystallization.

The ondansetron may optionally be further purified by crystallization according to a preferred procedure that is illustrated without limitation in Examples 3 and 4. According to the preferred crystallization procedure, the ondansetron prepared by contacting a 1,2,3,9-tetrahydrocarbazol-4-one of formula (II) with 2-methylimidazole in a solvent system comprising water and N,N-dimethylformamide is taken up in an alcohol solvent, the resulting solution is contacted with an adsorbent, the adsorbent is separated from the solution and then ondansetron is crystallized from the solution. The crystallization procedure may be repeated at least twice with continued improvement in the purity of the product.

Methanol is a preferred alcohol for the crystallization procedure and it is preferably used in an amount of from about 30 to about 50 milliliters per gram of ondansetron, more preferably about 40 milliliters per gram. At these concentrations, it is desirable to warm the alcohol to accelerate dissolution of the ondansetron.

Charcoal is a preferred adsorbent for the crystallization process and it is preferably used in weight ratio of from about 0.01 to about 0.1 with respect to the ondansetron, more preferably about 0.05.

After contacting the solution, preferably with agitation, for a period of time sufficient to adsorb a substantial portion of the exomethylene carbazolone, which is typically about 15 minutes, the adsorbent can be removed conventionally, e.g. by filtration.

Purified or partially-purified ondansetron can be obtained by crystallization from the alcohol directly by cooling or evaporation of the alcohol. As a practical matter, it is preferred to accelerate crystallization of the ondansetron by partially evaporating the alcohol and then cooling the residual solution. The ondansetron obtained by crystallization according to this procedure should have a substantially reduced exomethylene carbazolone content, preferably a reduction of 50% or more.

By practice of the present invention ondansetron can be obtained essentially free of the exomethylene carbazolone, more preferably, with an exomethylene carbazolone content of about 1% or less, yet more preferably with an exomethylene carbazolone content about 0.25% or less and most preferably with an exomethylene carbazolone content about 0.03% or less. The technique for measuring the purity ondansetron obtained by practice of the present invention is taught in the introductory portion of the Examples.

Ondansetron prepared by contacting a 1,2,3,9-tetrahydrocarbazol-4-one of formula (II) with 2-methylimidazole in a solvent system comprising water and N,N-dimethylformamide, and optionally further purified according to the procedure just described, may be incorporated into a pharmaceutical product such as orally disintegrating tablets. Orally disintegrating tablets can be formulated according to methods known in the art using pharmaceutical excipients that disperse or dissolve in saliva and do not retain the drug in solid form. Such excipients include gelatin and mannitol, and may further include antimicrobial agents such as methylparaben and propyl paraben and sweetening agents and flavoring agents such as aspartame, and strawberry flavor.

The isolated ondansetron also may be converted to a pharmaceutically acceptable acid addition salt using techniques well known in the art. Acids from which an acid addition salt can be made include hydrochloric acid, maleic acid, citric acid, tartaric acid, methansulfonic acid and benzensulfonic acid, to name but a few. To illustrate such well known processes, ondansetron may be taken up in diethyl ether. To the solution is added one molar equivalent of ethereal HCl. The salt forms essentially instantaneously and owing to its ionic character is poorly soluble in ether and precipitates from the solution whereupon it can be separated from the solution by filtration, decantation, centrifugation and the like. Other techniques for converting ondansetron to its hydrochloride salt, which is obtained as a dihydrate, are disclosed in U.S. Pat. No. 6,388,091 (See Examples 4, 5 and 10), which patent is hereby incorporated by reference in its entirety and in particular for its teaching of techniques for converting ondansetron to its hydrochloride salt dihydrate. Among the techniques disclosed therein, is the following. Ondansetron is suspended in a 10:1 mixture of ethanol: water. 6 N HCl was slowly added to the suspension at 10° C. After 3 h at that temperature the mixture was filtered to obtain ondansetron hydrochloride dihydrate.

Pharmaceutically acceptable ondansetron acid addition salts made by the process of this invention also may be incorporated into pharmaceutical products for administration to a patient in need of suppression of vomiting. Such pharmaceutical products include compressed tablets, in which the ondansetron acid addition salt is dispersed in a pharmaceutical vehicle. Pharmaceutical vehicles contain one or more excipients or adjuvants such as diluents, e.g. microcrystalline cellulose, lactose, hydroxypropylmethyl cellulose and the like; disintegrants, e.g. pregelatinized starch, croscarmellose sodium, crospovidone, sodium starch glycolate and the like; humectants e.g. triacetin, glycerol and the like; colorants, e.g. titanium dioxide, iron oxide yellow or iron oxide red; flavorings and the like. Such pharmaceutical products further include oral solutions in which the ondansetron salt is dissolved in an aqueous vehicle, optionally with viscosity modifiers, e.g. corn syrup; antimicrobial agents, e.g. sodium benzoate; buffering agents e.g. citric acid and sodium citrate; and flavoring agents e.g. strawberry flavoring. Such pharmaceutical products further include solutions for injection wherein the ondansetron or ondansetron salt is dissolved in an aqueous or oily medium, optionally with an antimicrobial agent, and packaged in a single dose or multi-dose container.

The starting materials used in the process of this invention are available from commercial sources and/or readily accessible by published synthetic procedures. 1,2,3,9-Tetrahydrocarbazole-4-one (IIa) is commercially available from Ningbo Free Trade Zone Sinolite Industrial Co. Ltd. (Ningbo, China) and Aryl SA (Buenos Aires, Argentina). Generally, 1,2,3,9-tetrahydrocarbazol-4-ones of formula (II) can be prepared by reactions that are well known in the art. One such method is by a Mannich reaction of a 1,2,3,9-tetrahydrocarbazole-4-one of formula (XV)

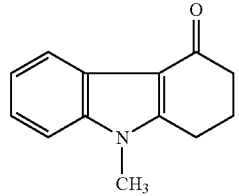

(XV)

with formaldehyde and a secondary amine of formula $HNR_1R_2$. 1,2,3,9-Tetrahydrocarbazole-4-ones of formula (XV) in turn may be prepared by the method described in H. Iida et al., *J. Org. Chem*, 1980, 45, 2938–42, which is hereby incorporated by reference in its entirety.

2-Methylimidazole is commercially available from variety of sources including Aldrich Chemical Company (2003–2004 cat. No. M5,085-0) and Merck (Darmstadt, Germany) (Prod. No. 818964).

Having thus described the present invention with reference to certain preferred embodiments, it will now be further illustrated with specific Examples employing the process. It is intended that the specification, including the examples, be considered illustrative only, with the scope of the invention being determined by the claims that follow the Examples.

EXAMPLES

General

3-[(Dimethylamino)methyl]-1,2,3,9-tetrahydro-9-methyl-4H-carbazol-4-one hydrochloride was purchased from Aryl SA. 2-Methylimidazole was purchased from Merck. Both starting materials were used as received from the supplier. Water and DMF were reagent grade and were used as received. Product purity was determined by reverse phase high performance liquid chromatography using the following conditions:

Column: Hypersyl BDS C-18 reverse phase column
Eluent: Phosphate buffer to pH 3.5 in acetonitrile-methanol mixture
Flow rate: 1.2 ml min$^{-1}$
Detection: UV, $\lambda$=216 nm
Column Temp.: 25° C.
Injection Volume: 10 μl
Run time: 50 min.

Preparation of 1,2,3,9-Tetrahydro-9-methyl-3-[(2-methyl-1H-imidazol-1-yl)methyl]-4H-carbazol-4-one

Example 1

3-[(Dimethylamino)methyl]-1,2,3,9-tetrahydro-9-methyl-4H-carbazol-4-one hydrochloride (10 g, 34 mmol) and 2-methylimidazole (16.8 g, 205 mmol, 6.0 eq.) were suspended in mixture of water (75 ml) and dimethyl formamide (37.5 ml). The reaction mixture was heated to reflux (102–103° C.) and stirred for a further 6 hours at this temperature. The reaction mixture was cooled to 5–10° C. and stirred for half an hour at this temperature. The precipitated crude ondansetron base was filtered and washed with cold water (3×90 ml) and dried under vacuum at 60° C. to give ondansetron base (9.68 g, 96.4% yield) in 98.9% HPLC purity.

Example 2

3-[(Dimethylamino)methyl]-1,2,3,9-tetrahydro-9-methyl-4H-carbazol-4-one hydrochloride (12 kg, 41 mol) and 2-methylimidazole (20.2 kg, 246 mol, 6 eq.) were suspended in mixture of water (120 L) and DMF (30 L). The reaction mixture was heated to reflux (100–102° C.) and stirred for 5 hours at this temperature. The reaction mixture was cooled to 5–10° C. and stirred for half an hour. The precipitated crude ondansetron base was filtered and washed with cold water (2×110 L) and dried under vacuum at 60° C. to give ondansetron base (10 kg, 83% yield) in 97.3% HPLC purity. The major impurity was the exomethylene carbazolone which amounted to 2.6% of the crude ondansetron mixture.

Recrystallization of Crude 1,2,3.9-Tetrahydro-9-methyl-3-[(2-methyl-1H-imidazol-1-yl)methyl]-4H-carbazol-4-one

Example 3

The crude ondansetron mixture prepared as described in Example 2 (11.7 g) was dissolved in methanol (468 ml) at 62° C. The resulting solution was stirred over charcoal (0.6 g) at 62° C. for 15 min. and then the charcoal was filtered off. An approximately 100 ml portion of the methanol was distilled off under reduced pressure. The solution was then cooled to 0–5° C. and stirred for an hour. Precipitated crystals were filtered off and washed twice with cold (0–5° C.) methanol (7.3 ml). Crystals were dried under reduced pressure at 65° C. to give ondansetron (~81%, yield) in an HPLC purity of 99.6% and with 0.25% contamination by the exomethylene carbazolone.

Example 4

Crystallized ondansetron prepared as described in Example 3 (9.5 g) was dissolved in methanol (380 ml) at 62° C. The solution was stirred over charcoal at 62° C. for 15 min. and then the charcoal was filtered off. An approximately 95 ml portion of methanol was distilled off. the solution was then cooled to 0–5° C. and stirred for an hour. Precipitated crystals were filtered off and washed twice with cold (0–5° C.) methanol (5.9 ml). The crystals were then dried under reduced pressure at 65° C. to give ondansetron (~81% yield) in 99.9% HPLC purity and with an exomethylene carbazolone content of 0.03%.

Having thus described the invention with respect to certain preferred embodiments and further illustrated it with examples, those skilled in the art may come to appreciate substitutions and equivalents that albeit not expressly described are taught and inspired by this invention. Whereas such substitutions and equivalents do not depart from the spirit of the invention they are within its scope which is defined by the claims which follow.

What is claimed is:

1. A process for preparing 1,2,3,9-tetrahydro-9-methyl-3-[(2-methyl-1H-imidazol-1-yl)methyl]-4H-carbazol-4-one comprising contacting 3-[(dialkylamino) methyl]-1,2,3,9-tetrahydro-9-methyl-4H-carbazol-4-one of formula (II)

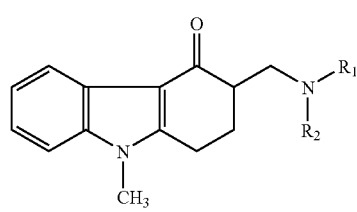

(II)

or salt thereof and 2-methylimidazole in a solvent system comprising water and N,N-dimethylformamide, wherein substituents $R_1$ and $R_2$ are independently selected from $C_1$–$C_6$ linear, branched and cyclic alkyl groups.

2. The process of claim 1, wherein the 3-[(dialkylamino) methyl]-1,2,3,9-tetrahydro-9 methyl-4H-carbazol-4-one of formula (II) is 3-[(dimethylamino)methyl]-1,2,3,9 tetrahydro-9-methyl-4H-carbazol-4-one.

3. The process of claim 1, wherein the salt of 3-[(dialkylamino)methyl]-1,2,3,9-tetrahydro-9 methyl-4H-carbazol-4-one of formula (II) is 3-[(dimethylamino)methyl]-1,2,3,9-tetrahydro-9-methyl-4H-carbazol-4-one hydrochloride.

4. The process of claim 1, wherein about 10 to about 40 percent by volume of the solvent system is N,N-dimethylformamide.

5. The process of claim 4, wherein about 20 to about 33 percent by volume of the solvent system is N,N-dimethylformamide.

6. The process of claim 1, wherein about 50 to about 90 percent by volume of the solvent system is water.

7. The process of claim 6, wherein about 66 to about 80 percent by volume of the solvent system is water.

8. The process of claim 1, wherein contacting occurs by adding the 3-[(dialkylamino)methyl]-1,2,3,9-tetrahydro-9-methyl-4H-carbazol-4-one and 2-methylimidazole to the solvent system resulting in a heterogeneous mixture and heating the solvent system to form a homogeneous mixture.

9. The process of claim 8, wherein the solvent system is heated at a temperature of from about 95° C. to about 110° C.

10. The process of claim 8, wherein the solvent system is heated at reflux temperature.

11. The process of claim 1 wherein the 3-[(dialkylamino)methyl]-1,2,3,9-tetrahydro-9-methyl-4H-carbazol-4-one is contacted with from about 2 to about 6 molar equivalents of 2-methylimidazole.

12. The process of claim 1 wherein the concentration of 3-[(dialkylamino)methyl]-1,2,3,9-tetrahydro-9-methyl-4H-carbazol-4-one is from about 0.2 to about 0.5 moles per liter of the solvent system.

13. The process of claim 1 further comprising:
a) separating the 1,2,3,9-tetrahydro-9-methyl-3-[(2-methyl-1H-imidazol-1-yl)methyl]-4H-carbazol-4-one from the solvent system;
b) forming a solution of the 1,2,3,9-tetrahydro-9-methyl-3-[(2-methyl-1H-imidazol-1-yl)methyl]-4H-carbazol-4-one in an alcohol;
c) contacting the solution with an adsorbent;
d) separating the adsorbent from the solution; and
e) crystallizing 1,2,3,9-tetrahydro-9-methyl-3-[(2-methyl-1H-imidazol-1-yl)methyl]-4H-carbazol-4-one from the solution.

14. The process of claim 13 further comprising repeating steps (b)–(e).

15. The process of claim 13 wherein the alcohol is methanol.

16. The process of claim 13 wherein the adsorbent is charcoal.

17. The process of claim 1 further comprising converting the 1,2,3,9-tetrahydro-9-methyl-3-[(2-methyl-1H-imidazol-1-yl)methyl]-4H-carbazol-4-one into a pharmaceutically acceptable salt.

18. The process of claim 17 wherein the pharmaceutically acceptable salt is a hydrochloride salt.

19. The process of claim 18 wherein the hydrochloride salt is a dihydrate.

20. A process for preparing 1,2,3,9-tetrahydro-9-methyl-3-[(2-methyl-1H-imidazol-1-yl)methyl]-4H-carbazol-4-one comprising:
a) contacting a 3-[(dialkylamino)methyl]-1,2,3,9-tetrahydro-9-methyl-4H-carbazol-4-one of formula (II)

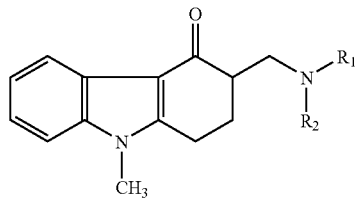

(II)

or salt thereof wherein substituents $R_1$ and $R_2$ are independently selected from $C_1$–$C_6$ linear, branched and cyclic alkyl groups, and 2-methylimidazole in a solvent system comprising the components water and N,N,-dimethylformamide,
b) separating the 1,2,3,9-Tetrahydro-9-methyl-3-[(2-methyl-1H-imidazol-1-yl)methyl]-4H-carbazol-4-one from the solvent system,
c) forming a solution of the 1,2,3,9-Tetrahydro-9-methyl-3-[(2-methyl-1H-imidazol-1-yl)methyl]-4H-carbazol-4-one in methanol,
d) contacting the solution with charcoal,
e) separating the charcoal from the solution, and
f) crystallizing 1,2,3,9-Tetrahydro-9-methyl-3-[(2-methyl-1H-imidazol-1-yl)methyl]-4H-carbazol-4-one from the solution.

21. A process for preparing 1,2,3,9-tetrahydro-9-methyl-3-[(2-methyl-1H-imidazol-1-yl)methyl]-4H-carbazol-4-one comprising:
a) forming a mixture by contacting in any order
i) a 3-[(dialkylamino)methyl]-1,2,3,9-tetrahydro-9-methyl-4H-carbazol-4-one of formula (II)

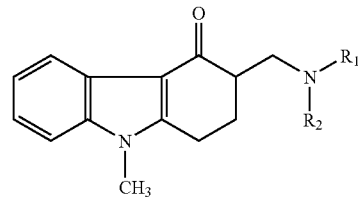

(II)

or salt thereof wherein substituents $R_1$ and $R_2$ are independently selected from $C_1$–$C_6$ linear, branched and cyclic alkyl groups,
ii) from about 2 to about 6 molar equivalents of 2-methylimidazole with respect to the 3-[(dialkylamino)methyl]-1,2,3,9-tetrahydro-9-methyl-4H-carbazol-4-one,
iii) a quantity of N,N-dimethylformamide, and
iv) water in a quantity of about 2 to about 4 times the quantity of N,N-dimethylformamide on a volume basis,
wherein the total quantity of water and N,N-dimethylformamide is from about 2 to about 5 liters per mole of the 3-[(dialkylamino)methyl]-1,2,3,9-tetrahydro-9-methyl-4H-carbazol-4-one,
b) heating the mixture to from about 95° C. to about 110° C. for a period of time sufficient to substantially convert the 3-[(dialkylamino)methyl]-1,2,3,9-tetrahydro-9-methyl-4H-carbazol-4-one to 1,2,3,9-tetrahydro-9-methyl-3-[(2-methyl-1H-imidazol-1-yl)methyl]-4H-carbazol-4-one,
c) cooling the mixture to induce crystallization of the 1,2,3,9-tetrahydro-9-methyl-3-[(2-methyl-1H-imidazol-1-yl)methyl]-4H-carbazol-4-one, and
d) separating the N,N-dimethylformamide, water and unreacted 2-methylimidazole from the 1,2,3,9-tetrahydro-9-methyl-3-[(2-methyl-1H-imidazol-1-yl)methyl]-4H-carbazol-4-one.

22. The process of claim 1, further comprising:
a) heating at a temperature of from about 95° C. to about 110° C. for a period of time sufficient to substantially convert the 3-[(dialkylamino)methyl]-1,2,3,9-tetrahydro-9-methyl-4H-carbazol-4-one to 1,2,3,9-tetrahydro-9-methyl-3-[(2-methyl-1H-imidazol-1-yl)methyl]-4H-carbazol-4-one;
b) cooling to crystallize the 1,2,3,9-tetrahydro-9-methyl-3-[(2-methyl-1H-imidazol-1-yl)methyl]-4H-carbazol-4-one; and
c) separating the crystallized 1,2,3,9-tetrahydro-9-methyl-3-[(2-methyl-1H-imidazol-1-yl)methyl]-4H-carbazol-4-one.

* * * * *